(12) United States Patent
Fujii

(10) Patent No.: US 8,040,375 B2
(45) Date of Patent: Oct. 18, 2011

(54) METHOD AND APPARATUS FOR INSPECTING SLIDER USING MOVING STAGE

(75) Inventor: Ryuji Fujii, Hong Kong (CN)

(73) Assignee: SAE Magnetics (H.K.) Ltd., Hong Kong (CN)

( * ) Notice: Subject to any disclaimer, the term of this patent is extended or adjusted under 35 U.S.C. 154(b) by 1141 days.

(21) Appl. No.: 11/819,032

(22) Filed: Jun. 25, 2007

(65) Prior Publication Data

US 2007/0296812 A1 Dec. 27, 2007

(30) Foreign Application Priority Data

Jun. 27, 2006 (JP) .................................. 2006-176617

(51) Int. Cl.
*G01N 21/00* (2006.01)
(52) U.S. Cl. ....... 348/92; 348/87; 356/237.4; 356/237.5
(58) Field of Classification Search ............... 348/86, 348/87, 92; 356/237.3, 273.3, 237.4, 237.5
See application file for complete search history.

(56) References Cited

U.S. PATENT DOCUMENTS

| 6,501,545 B2* | 12/2002 | Komuro et al. ............ 356/237.2 |
| 7,129,484 B2* | 10/2006 | Hwu ............................. 250/307 |
| 7,147,539 B1* | 12/2006 | Hao et al. ......................... 451/5 |

FOREIGN PATENT DOCUMENTS

| JP | 05-223534 | 8/1993 |
| JP | 2002-48716 | 2/2002 |

* cited by examiner

*Primary Examiner* — Viet Vu
(74) *Attorney, Agent, or Firm* — Nixon & Vanderhye PC

(57) ABSTRACT

A method for inspecting a slider having a substantially rectangular parallelepiped shape is provided. The method has: a lifting step of lifting said slider upward and stopping said slider at an inspecting position while supporting said slider at an undersurface of said slider, wherein said undersurface is a surface that is other than a first surface, said first surface being an air bearing surface or a surface that is to be formed in said air bearing surface; and an inspection step of simultaneously inspecting said first surface and a second surface of said slider, said second surface being a surface that is other than said first surface and said undersurface, wherein said first surface is inspected by a first camera and said second surface is inspected by a second camera, said first and second cameras being arranged in advance such that an optical axis thereof passes through said inspecting position.

19 Claims, 6 Drawing Sheets

METHOD AND APPARATUS FOR INSPECTING SLIDER USING MOVING STAGE

The present application is based on, and claims priority from, J.P. Application No. 2006-176617, filed on Jun. 27, 2006, the disclosure of which is hereby incorporated by reference herein in its entirety.

BACKGROUND OF THE INVENTION

1. Field of the Invention

The present invention relates to a method and an apparatus for inspecting a slider, and particularly relates to a method and an apparatus for optically inspecting a slider that is used for a hard disk drive.

2. Description of the Related Art

A slider is produced by forming a write element and a read element on a ceramics wafer, such as an AlTiC wafer, by means of the thin-film technology, then by dicing the wafer into bars such that the surface of the bar that is to be formed in an air bearing surface extends in the longitudinal direction of the bar, and further by dicing the bar into individual sliders. When a write element and a read element are formed on a wafer, the identification number of each slider is written on the top surface of the layers that are deposited, and the sliders are controlled by the identification numbers after the wafer is diced. After the sliders are separated from the wafer by dicing, each slider is subjected to visual inspections several times using an optical microscope or the like. The inspections are performed when the slider is included in a bar, when slider has been separated from the bar, and also when the slider has been incorporated in a head gimbal assembly (HGA). If the inspection is performed only at the final stage at which the slider has been incorporated into an HGA, then yield loss is increased, and investigation to determine the cause of defects cannot be performed effectively. Therefore, it is very important to perform inspection at each process in order to identify yield loss at each step, to identify the cause of defect, and to provide improvement in the process.

Visual inspection is performed mainly in order to find adhesion of dust to the air bearing surface or to the surface that is to be formed in the air bearing surface by means of lapping (hereinafter, called a first surface) and to find chippings on the first surface. However, it is necessary to simultaneously inspect the top surface of the layers together when the first surface is inspected because the slider number is written on the top surface of the layers. Further, in order to manage the manufacturing process of the bar, the slider number needs to be checked at each step. Indeed, the top surface of the layers is more frequently checked than the first surface. The slider number is checked by a microscope. In order to identify each slider, both the wafer number and the slider number are required. The wafer number is often written on the surface that is opposite to the top surface of the layers, i.e., on the back surface of the wafer. In this case, three surfaces in total including the first surface need be inspected by means of a microscope. In this specification, inspection of the slider means not only checking and inspecting the first surface and other surfaces, as well as performing visual inspections of the slider, but also merely checking the slider number and the wafer number.

Incidentally, since a bar is highly brittle, it is normally stored and conveyed in a case, or in a tray. FIG. 1 shows an exemplary tray which has been conventionally used. Tray 121 is made of a frame, in which a plurality of bars can be simultaneously stored. Stepped portions 123 are provided at two sides of the tray that are opposite to each other, and bars B are held by stepped portions 123. Since the slider numbers are frequently checked, as described above, bars B are held such that the top surface of the layers, on which the slider numbers are written, faces upward so that the slider numbers can be easily checked.

When the visual inspection of the first surfaces is performed, the slider numbers are first checked with an optical microscope in a state in which the bars are held in the tray. If the wafer number is written on the back surface of the wafer, then the tray is turned upside down in order to check the wafer number. Next, the bar is removed from the tray one by one by using tweezers, then conveyed to an inspection table on which an optical microscope is installed, and the first surfaces are inspected. However, the quality and efficiency of the inspection significantly depend on the skill (skill of positioning the bar, inspection time, etc.) of the operator, and there is large variability in the level of skill among the operators. Since the bar is bristle, the operation of removing a bar from a tray and of returning the bar to the tray after inspection requires immense skill, and damage to the bar that is caused by an operational error or by adhesion of contaminants to the bars frequently takes place, which leads to a reduction in yield and an increase in inspection time. If a defect is found on the first surface, then the bar is turned by 90 degrees to check the slider number again in order to identify the slider. If many defects are found, then the inspection time is increased. In order to shorten the inspection time, a larger number of operators are required.

In order to address the problem mentioned above, efforts have been made to rationalize the method for inspecting a slider. Japanese Patent Laid-Open Publication No. 223534/93 discloses a method for inspecting a slider in which a slider is inspected from a plurality of directions. Specifically, many slides are fixed to the outer peripheral surface of a rotating support element. The orientation of the sliders is changed in accordance with the rotation of the support element. A visual inspection is performed by means of a fixed camera. It is also disclosed that sliders are fixed to a tape in advance and then the tape is wound on the support element in order to fix the slider.

Japanese Patent Laid-Open Publication No. 2002-048716 discloses a method for simultaneously inspecting a plurality of surfaces of a slider by using mirrors. Specifically, mirrors each having angles of 45 degrees are arranged on the sides of a slider which is to be inspected. By arranging the mirrors within the field of view of an optical microscope, the images of the sides of the slider, which are the reflections in the mirrors, as well as the slider itself, come into the field of view of the optical microscope so as to allow the state of the sides, as well as the front surface, of the slider to be simultaneously inspected.

However, the conventional art which is disclosed in these patent documents is disadvantageous with regard to operation efficiency because the prior art requires separating a slider from a bar by dicing and then fixing the slider that is separated onto a special support tool. If adhesive is used to attach a slider to the support tool, then the adhesive may remain on the slider, and reliability of the slider may deteriorate.

SUMMARY OF THE INVENTION

An object of the present invention is to provide a method and an apparatus which allows visual inspection of a slider in an efficient manner while limiting influence on the slider.

According to an embodiment of the present invention, a method for inspecting a slider having a substantially rectangular parallelepiped shape is provided. The method comprises: a lifting step of lifting said slider upward and stopping said slider at an inspecting position while supporting said slider at an undersurface of said slider, wherein said undersurface is a surface that is other than a first surface, said first surface being an air bearing surface or a surface that is to be formed in said air bearing surface; and an inspection step of simultaneously inspecting said first surface and a second surface of said slider, said second surface being a surface that is other than said first surface and said undersurface, wherein said first surface is inspected by a first camera, said first camera being arranged in advance such that an optical axis of said first camera passes through said inspecting position, and wherein said second surface is inspected by a second camera, said second camera being arranged in advance such that an optical axis of said second camera passes through said inspecting position.

As described above, according to the method for inspecting a slider of the present invention, a slider is lifted up to a predetermined inspecting position while being supported at the undersurface of the slider. Specifically, since the slider is supported only by gravity, the step of fixing the slider to a special jig in advance is not required. Since the undersurface at which the slider is supported is a surface that is other than the first surface, undesired force against the first surface or adhesion of contaminants to the first surface during inspection is not likely to occur. Therefore, the air bearing surface can be easily protected.

The inspection step may comprise simultaneously inspecting the first surface and a third surface of the slider, the third surface being a surface that is other than the first surface, the undersurface, and the second surface, wherein the first surface is inspected by the first camera, and wherein the third surface is inspected by a third camera, the third camera being arranged in advance such that an optical axis of the third camera passes through the inspecting position.

The lifting step may comprise moving an assembly of the sliders upward and stopping the assembly at the inspecting position, wherein the sliders are aligned in a longitudinal direction of the assembly. The method may further comprise, after the inspection step; a step of moving the assembly in the longitudinal direction of the assembly so that a slider that has not yet been inspected moves to the inspecting position, and repeating the inspection step for the slider which moves to the inspecting position.

The assembly may be a bar in which a plurality of sliders are formed.

The lifting step may comprise; disengaging the bar from a support element and lifting the bar upward by causing a moving stage to abut on an undersurface of the bar and by moving the moving stage upward, wherein the bar is only supported on the support element at both end portions of the bar by self weight thereof, and wherein the method further comprises; a step of lowering the moving stage and causing the bar to be supported on the support element after the inspection step.

The assembly may have a plurality of sliders which are separated from a bar by means of dicing, the bar having a plurality of sliders, wherein the sliders are held together by a dicing jig after dicing.

The lifting step may comprise disengaging the slider from a tray in which the slider is stored and lifting the slider upward by causing a moving stage to abut on the undersurface of the slider and further by moving the moving stage upward, wherein the tray has a through-hole on a bottom surface thereof, and wherein the moving stage abuts on the undersurface of the slider through the through-hole, and wherein the method further comprises a step of lowering the moving stage and storing the slider in the tray after the inspection step.

The inspection step may comprise simultaneously displaying the surfaces of the slider on a single image display device, the surfaces being simultaneously inspected.

The slider may be supported so that the first surface faces upward.

The slider may be supported such that the second surface corresponds to a surface on which a slider number is written.

According to another embodiment of the present invention, an apparatus for inspecting a slider is provided. The apparatus comprises: a first stage which includes a support element, wherein a bar can be supported on said support element only at both end portions thereof by self weight of said bar, wherein said bar includes a plurality of sliders which are aligned in a longitudinal direction of said bar; a second stage which is vertically movable such that said second stage abuts on an undersurface of said bar from below and disengages said bar from said support element to lift said bar upward to an inspecting position; a first camera for obtaining an image of a first surface of said slider, said first surface being an air bearing surface or a surface that is to be formed in said air bearing surface, wherein said first camera is arranged in advance such that an optical axis thereof passes through said inspecting position; and a second camera for obtaining an image of a second surface of said slider, said second surface being a surface that is other than said first surface and said undersurface, wherein said second camera is arranged in advance such that an optical axis thereof passes through said inspecting position.

According to the apparatus for inspecting a slider of the present invention, a plurality of surfaces of a slider can be inspected in a state in which the slider is included in a bar, i.e., in the unit of a bar. It is not necessary to fix the sliders one by one to a jig for inspection, and thus, rationalization of inspection procedures is achieved. Since the undersurface on which the slider is supported is a surface that is other than the first surface, undesired force against the first surface or adhesion of contaminants to the first surface during inspection is not likely to occur.

The apparatus may further comprises: a third camera for obtaining an image of a third surface of the slider, the third surface being a surface that is other than the first surface, the undersurface, and the second surface, wherein the third camera is arranged in advance such that an optical axis of the third camera passes through the inspecting position.

The apparatus may further comprise: an image display device which is configured to simultaneously display the images which are obtained by the cameras.

The first camera may have more than one magnification.

The support element may have step portions which allow the bar to rest.

The support element may be configured to support the bar such that the first surface faces upward.

The first and second stages may be configured to travel a same distance in the longitudinal direction of the bar.

The support element may be configured to hold a plurality of bars such that the bars are held in parallel with each other, and the first stage may be configured to move in a direction that is perpendicular to the longitudinal direction in a horizontal plane.

According to yet another embodiment of the present invention, an apparatus for inspecting a slider is provided. The apparatus comprises: a tray for storing a slider, the tray including a through-hole on a bottom surface thereof; a moving stage which is vertically movable such that the moving stage abuts on an undersurface of the slider through the through-hole in order to disengage the slider from the tray to lift the slider upward to an inspecting position; a first camera for obtaining an image of a first surface of the slider, the first surface being an air bearing surface or a surface that is to be formed in the air bearing surface, wherein the first camera is arranged in advance such that an optical axis of the first camera passes through the inspecting position; and a second camera for obtaining an image of a second surface of the slider, the second surface being a surface that is other than the first surface and the undersurface, wherein the second camera is arranged in advance such that an optical axis of the second camera passes through the inspecting position.

As described above, according to the present invention, a method and an apparatus which allows visual inspection of a slider in an efficient manner while limiting the influence on the slider can be provided.

The above and other objects, features and advantages of the present invention will become apparent from the following description with reference to the accompanying drawings which illustrate examples of the present invention.

DETAILED DESCRIPTION OF THE INVENTION

Figure 1:
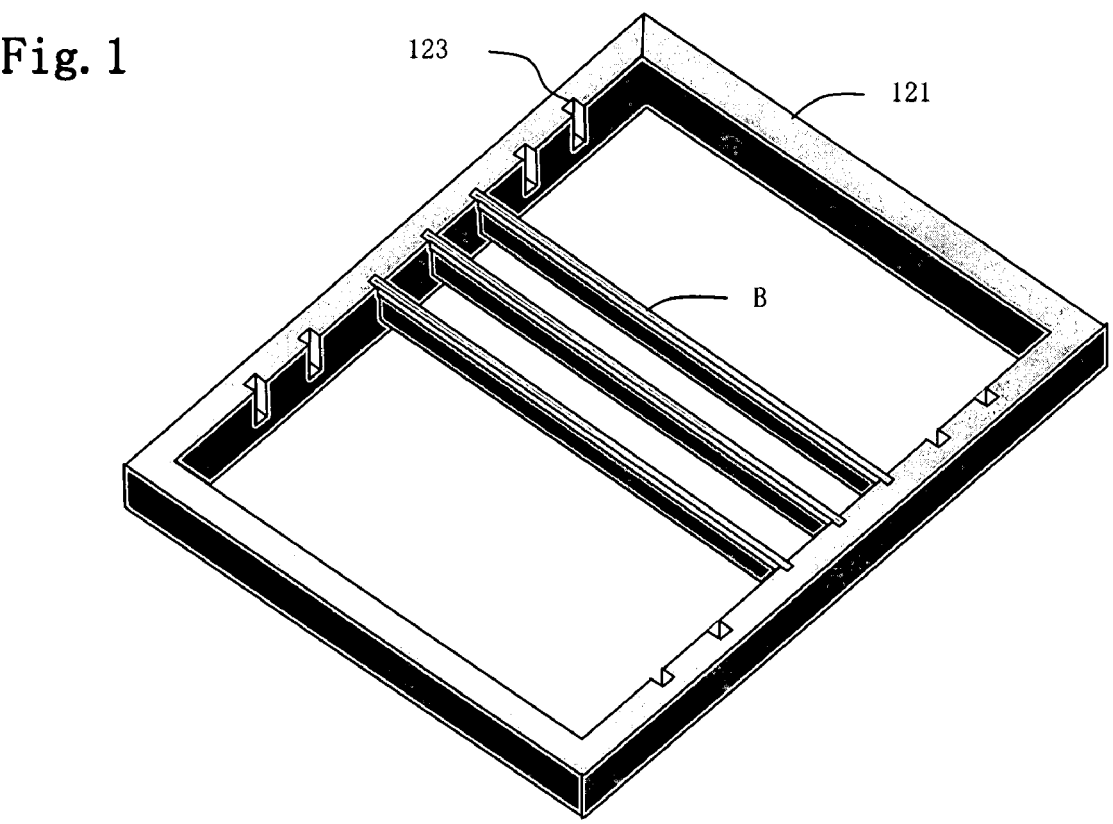
FIG. 1 is a perspective view of an exemplary tray according to prior art.
Figure 2:
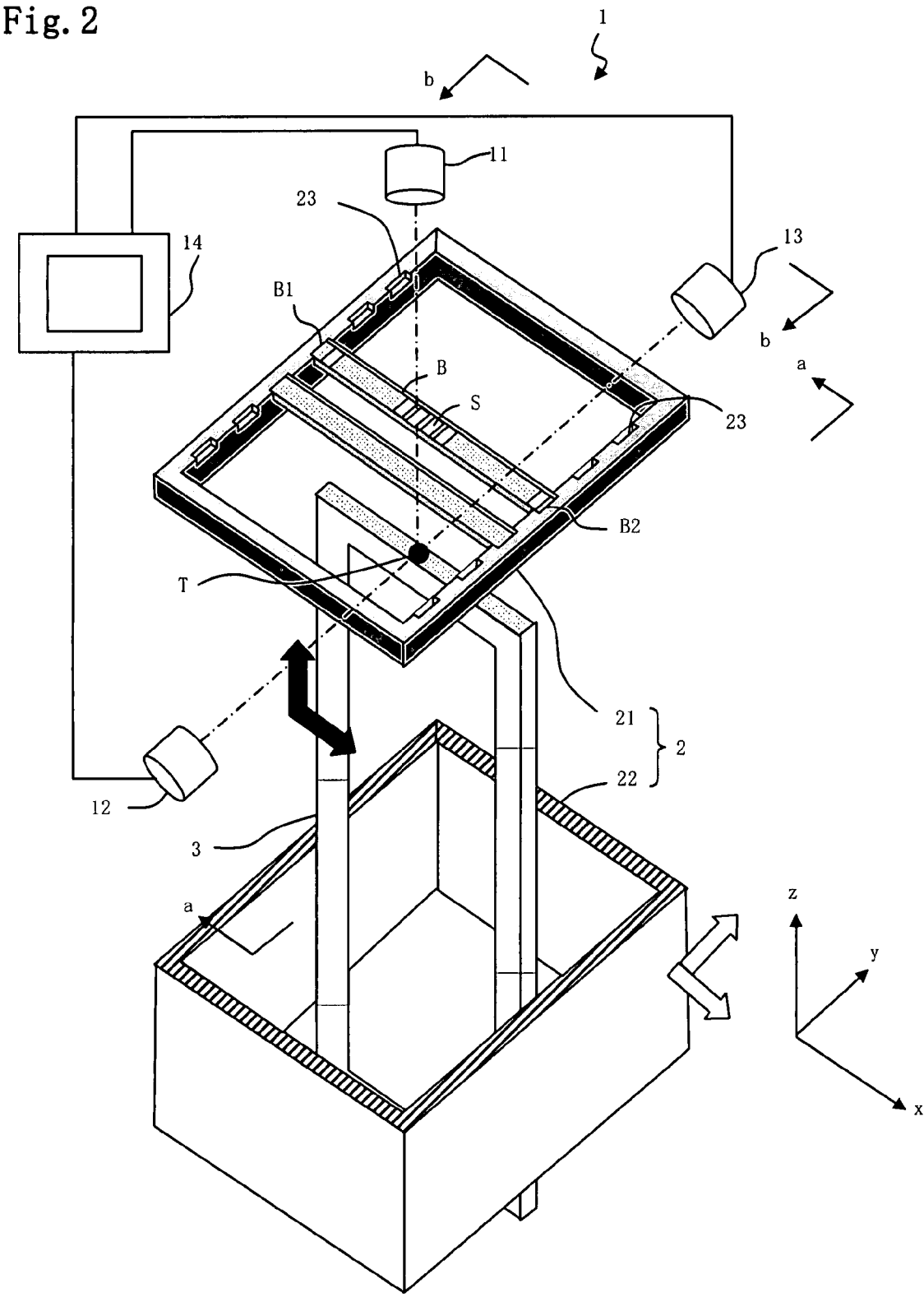
FIG. 2 is a diagram generally showing the configuration of an apparatus for inspecting a slider according to an embodiment of the present invention.

First, an apparatus for inspecting a slider according to an embodiment of the present invention will be described with reference to the drawing. FIG. 2 is a diagram generally showing the configuration of an apparatus for inspecting a slider according to an embodiment of the present invention. Apparatus 1 includes first stage 2, second stage 3, first to third cameras 11-13, and image display device 14 which displays image data that is obtained by first to third cameras 11-13. Cameras 11-13 are installed such that each of the optical axes thereof passes through inspecting position T.

First stage 2 has tray 21 for holding bar B, and base 22 for supporting tray 21. Tray 21 is detachably fixed to base 22 in an appropriate manner. Both tray 21 and base 22 are in the form of a frame, and tray 21 is fixed to the frame of base 22. Therefore, base 22 to which tray 21 is fixed has an opening. Tray 21 is configured such that bar B having many sliders S which are aligned in the longitudinal direction is supported by its own weight of bar B. Specifically, stepped portions 23 for holding bars B are provided on the two sides of tray 21 which are opposite to each other, and both end portions B1, B2 are configured to rest on stepped portions 23 so that bar B is supported by its own weight. Tray 21 may have the function of fixing bar B with a vacuum chuck. Tray 21 holds many bars B such that they are held in parallel with other.

Conveying means, not shown, is connected to base 22 in order to allow first stage 2 to move in longitudinal direction x of bar B and in direction y, which is perpendicular to direction x in the horizontal plane, as shown by the white arrows in the drawing.

Tray 21 also has the function of storing bar B. Therefore, tray 21 includes features that are similar to that of a conventional tray. However, tray 21 according to the present embodiment is constructed such that the first surface of the slider faces upward. Tray 21 is separately used in most of the manufacturing process of the sliders, and is only incorporated into apparatus 1 when visual inspection of the sliders is required.

Second stage 3, which is provided in the opening of first stage 2, is movable in vertical direction z so that second stage 3 abuts on the undersurface of bar B from below and that second stage 3 disengages bar B from tray 21 to convey bar B to inspecting position T. Second stage 3 can also move in longitudinal direction x of bar B together with first stage 2, as shown by the black arrow in the drawing.

First to third cameras 11-13 are provided above second stage 3. First camera 11 is arranged in advance such that the optical axis thereof passes through inspecting position T and such that first camera 11 faces downward in the vertical direction in order to obtain images of first surface M1 of the slider (see FIG. 4A). First surface M1 is the air bearing surface or the surface that is to be formed in the air bearing surface. First camera 11 can switch between a magnification of 200 and a magnification of 500 in order to inspect both the entire area of the first surface of the slider and the area in the vicinity of the element (pole) at appropriate magnifications.

Second camera 12 is also arranged in advance such that the optical axis thereof passes through inspecting position T and such that second camera 12 faces in the horizontal direction in order to obtain images of the top surface of the layers of the slider. Second camera 12 operates with a magnification of 200 in order to inspect the entire surface of the slider. It should be noted that the surface of the slider whose images are obtained by second camera 12 is not limited to the top surface of the layers of the slider. If the slider number is written on another surface, then second camera 12 is configured to obtain the images of that surface. If a specific surface of the slider needs to be inspected, second camera 12 is configured to obtain the images of that surface. In other words, the surface of the slider whose images is obtained by second camera 12 is second surface M2 which is one of the surfaces that are other than first surface M1 and the undersurface.

Third camera 13 is also arranged in advance such that the optical axis thereof passes through inspecting position T and such that third camera 13 faces in the horizontal direction in order to obtain images of the back surface of the slider (back side of the wafer). Third camera 13 operates with a magnification of 200 in order to inspect the entire back surface of the slider. Third camera 13 may be omitted if the image of the back side of the wafer is not required. It should be noted that the surface of the slider whose images is obtained by second camera 12 is not limited to the back surface of the slider. If a specific surface of the slider needs to be inspected, third camera 13 is configured to obtain the images of that surface. In other words, the surface of the slider whose images is obtained by third camera 13 is third surface M3 which is one of the surfaces that are other than first surface M1, the undersurface, and second surface M2 of the slider.

A digital camera that is loaded with, for example, but not limited to, CCDs (Charge-Coupled Devices) can be used as each of cameras 11-13. However, any type of image capturing means may be used. Similarly, the magnification is not limited to the ones described above. Further, a variable magnification is also applicable.

Each of cameras 11-13 is connected to image display device 14. Image display device 14 is capable of simultaneously displaying the image data that are captured by cameras 11-13 by, for example, dividing the display screen. Cameras 11-13 and image display device 14 may further be connected to a computer, not shown, for image processing and for image display.

Figure 3:
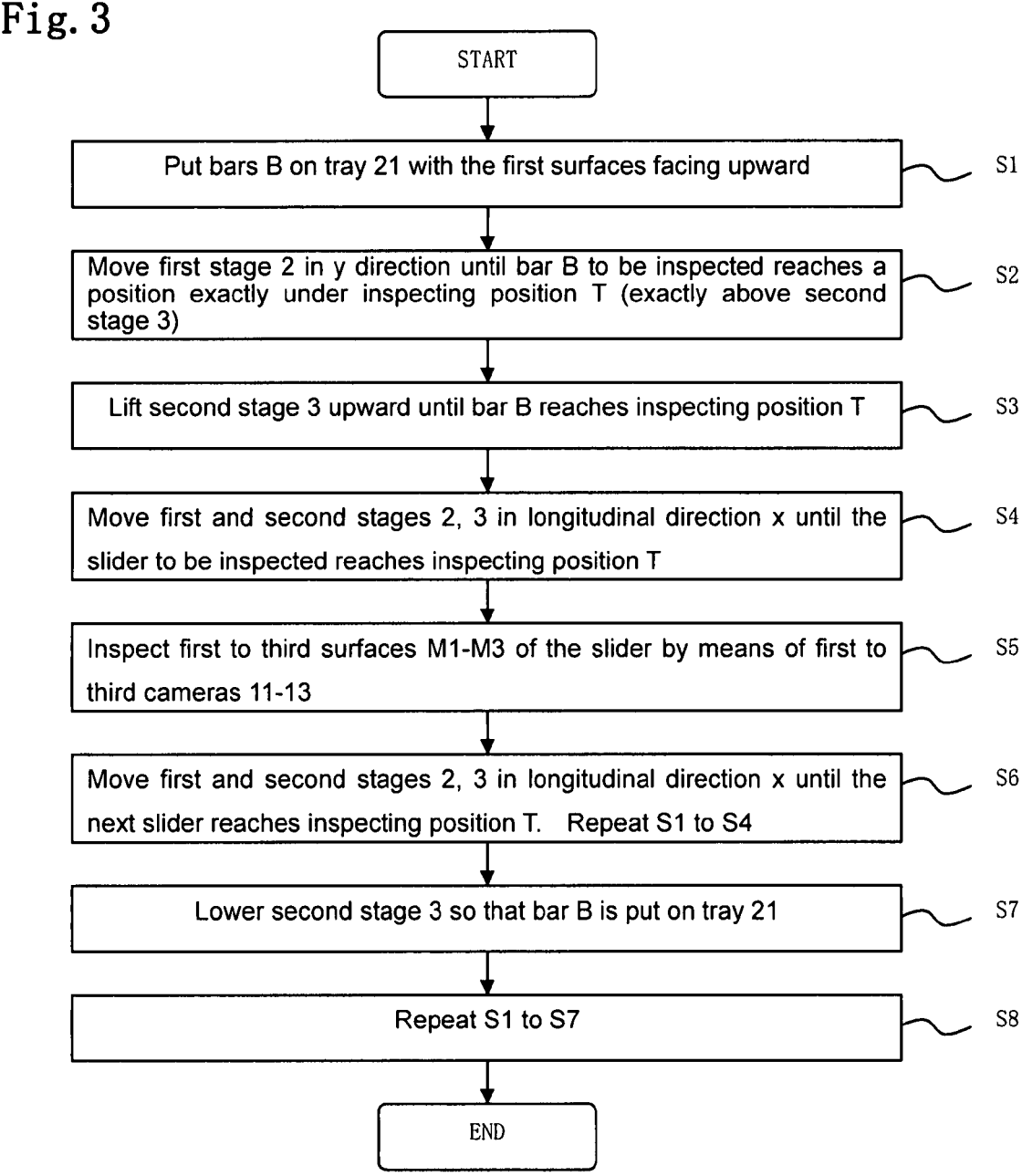
FIG. 3 is a flowchart in accordance with a method for inspecting a slider according to the present invention.
Figure 4A:
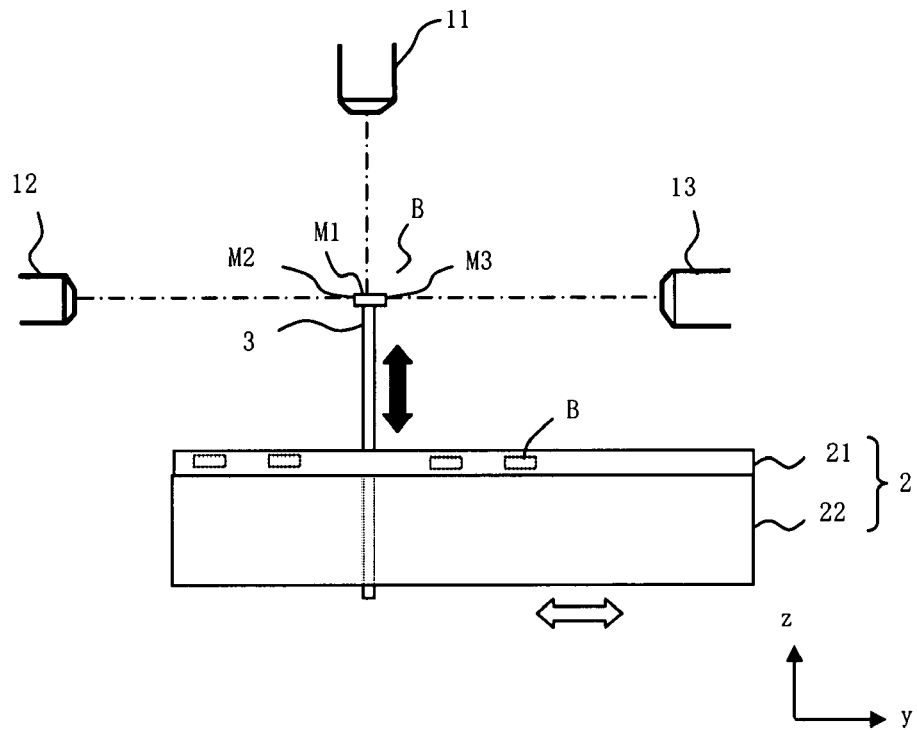
FIGS. 4A, 4B are schematic views showing a situation in which a slider is inspected, respectively.
Figure 4B:
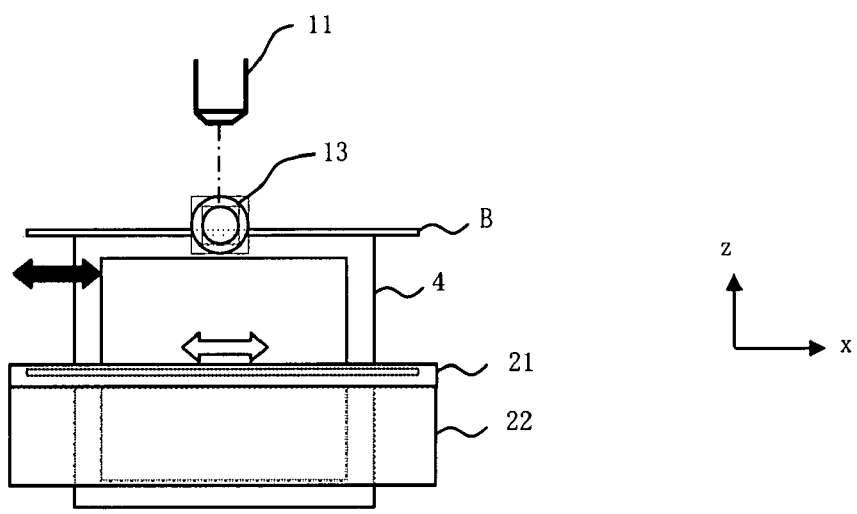

Next, a method for inspecting a slider using the inspection apparatus described above will be described with reference to the flowchart shown in FIG. 3. FIGS. 4A and 4B are schematic views showing situations in which a slider is inspected. FIG. 4A is a side view, seen from a-a direction in FIG. 2, and FIG. 4B is a side view, seen from b-b direction in FIG. 2.

(Step S1) First, a plurality of bars B which have been separated from the wafer by means of dicing are put on tray 21 with the first surfaces facing upward, as shown in FIG. 2. As described above, bar B is an assembly of slides in which a plurality of sliders are aligned in longitudinal direction x. The slider has a substantially rectangular parallelepiped shape. First surface M1, which is the air bearing surface, is formed on one of the surfaces of the slider. First surface M1 may also be the surface that is to be formed in the air bearing surface by means of lapping.

(Step S2) Next, first stage 2 is moved in y direction, as shown by the white arrow in FIG. 4A, until bar B that is to be inspected reaches a position that is exactly under inspecting position T (exactly above second stage 3).

(Step S3) Second stage 3 is lifted upward in this state. By raising second stage 3 through the inside space of base 22 in the direction that is shown by the black arrow in FIG. 4A, the upper end of second stage 3 abuts on the undersurface of bar B that is to be inspected. Second stage 3 continues to be lifted upward in the state in which the surface that is opposite to first surface M1 is supported by second stage 3, until bar B is stopped at inspecting position T. Since bar B is only supported on tray 21 at both end portions B1, B2 by its own weight, bar B is easily disengaged from tray 21 by causing the upper end of second stage 3 to abut on the undersurface of bar B and by further moving second stage 3 upward.

(Step S4) Next, as shown by the white arrow and the black arrow in FIG. 4B, first stage 2 and second stage 3 are moved in longitudinal direction x until they are stopped when the slider that is to be inspected moves to inspecting position T. First stage 2 and second stage 3 are adjusted in advance to travel the same distance in longitudinal direction x. It should be noted that the slider that is to be inspected may be moved to inspecting position T only by the movement of second stage 3. In this case, it is preferable that second stage 3 be configured to avoid interference with first stage 2.

(Step S5) First surface M1 of the slider is inspected by first camera 11 that is arranged in advance such that the optical axis thereof passes through inspecting position T. First camera 11 obtains an image of the entire area of first surface M1 and an enlarged image of the area in the vicinity of the pole while switching the magnification in an automatic or a manual operation. By observing the image of the entire area, the presence or absence of scratches or contaminants on first surface M1 can be detected. The area in the vicinity of the pole is important for the function of a slider, and therefore, inspection at a high magnification is required. It is possible to enhance the accuracy of the inspection because an image of a limited area is obtained at a high magnification. Simultaneously with the operation of first camera 11, the image of the entire area of second surface M2 is obtained by second camera 12 that is arranged in advance such that the optical axis thereof passes through inspecting position T. Second surface M2 may be, for example, the top surface of the layers on which the slider number is written. There is a large need to inspect the top surface of the layers because the top surface is also provided with bonding pads, not shown, and therefore, problems that are associated with contamination and chippings after cleaning may take place. Simultaneously, the image of the entire area of third surface M3 is obtained by third camera 13 that is arranged in advance such that the optical axis thereof passes through inspecting position T. Third surface M3 may be, for example, the back surface of the wafer (the surface that is opposite to the top surface of the layers). The wafer number is often written on this surface. It should be noted that "simultaneously", when obtaining an image or when performing inspection, is not limited to the literal sense and that the word includes the manner in which operations are successively performed at some intervals.

Figure 5:
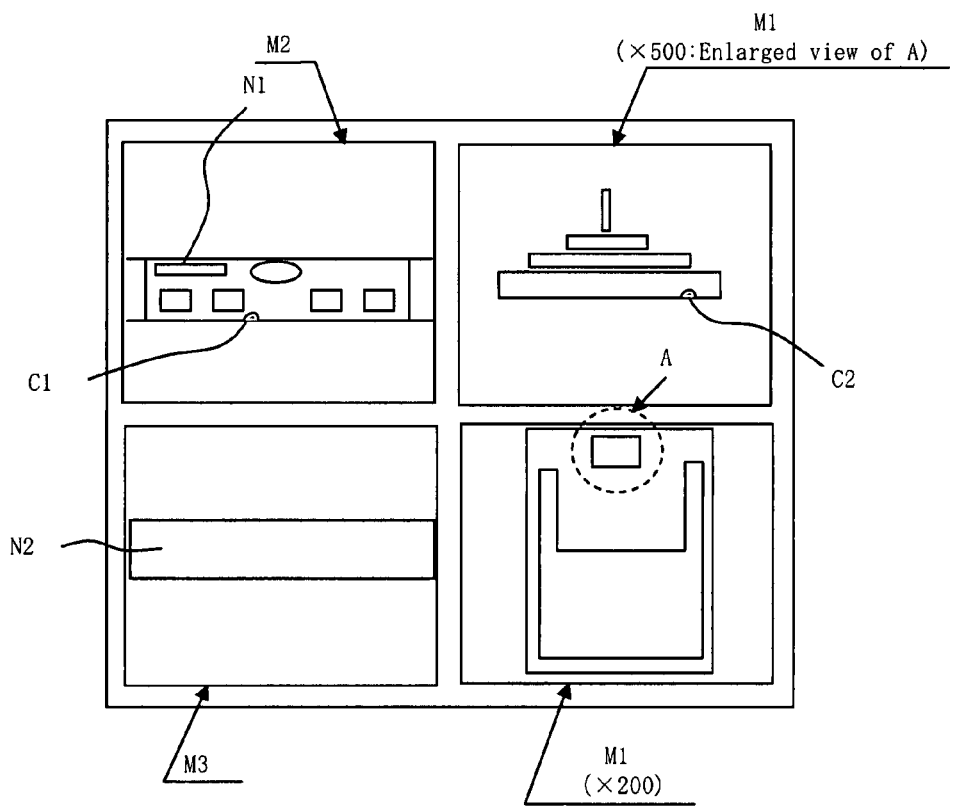
FIG. 5 is a conceptual diagram showing an image that is obtained by cameras and that is displayed on an image display device.

FIG. 5 is a conceptual diagram showing an image that is obtained by cameras and that is displayed on an image display device. The display screen of image display device 14 is divided into four sections. The image of the entire area of first surface M1 (lower right), the enlarged image of the area in the vicinity of the pole, which is designated by "A" in the drawing (upper right), the image of the entire area of second surface M2 (upper left), and the image of the entire area of third surface M3 (lower left) are simultaneously displayed on the respective sections. Since defects C1, C2, such as chippings, slider number N1, and wafer number N2 are simultaneously displayed, defects can be easily detected, and the slider is easily identified. Instead of simultaneously displaying four images, the images may be successively displayed on the entire display screen, or two or three images which are selected may be simultaneously displayed. If the image of third surface M3 is not required, then the operation itself of obtaining the image of third surface M3 using the camera may be omitted.

(Step S6) When the next slider is inspected, first stage 2 and second stage 3 are moved in longitudinal direction x so that bar B is moved in longitudinal direction x and that the next slider that is to be inspected moves to inspecting position T, as shown by the white arrow and the black arrow in FIG. 4B. Thereafter, step 5 is repeated for the sliders which move to inspecting position T.

(Step S7) When the inspection of bar B is finished, second stage 3 is lowered so that bar B is put on tray 21. As described above, bar B is only supported on tray 21 at both end portions B1, B2 by its own weight, bar B automatically returns to the original position of tray 21 by lowering second stage 3.

(Step S8) When another bar B is inspected, steps S2 to S7 described above are repeated as many times as required.

As described above, according to the method and the apparatus for inspecting a slider of the present embodiment, more than one surface of the slider can be simultaneously inspected in an efficient and highly reliable manner. Specifically, there is little possibility of damage to the air bearing surface, which may be caused by, for example, contact of tweezers during inspection, because the bar is moved upwardly in the vertical direction from the position at which the bar is stored in the tray, while the surface that is opposite to the air bearing surface is lifted up. Since the result of the inspection of each surface is simultaneously displayed on the image display device, it is easy to detect a slider that has a defect and, as a result, to enhance operation efficiency. Defects, such as chippings and contamination, on more than one surface that is to be inspected are often related to each other. Analysis and investigation to determine the cause of failures are facilitated because information on the inspection of more than one surface is simultaneously displayed. The need for installing many inspection apparatuses each having an optical microscope is reduced because of the improvement in operation efficiency. This will contribute to a reduction in the size of the area required for the operation.

In the present embodiment, it is possible to store the bar in the state in which the first surface of the slider faces upward. The present embodiment, which allows the bar to be stored in this manner, is advantageous because, in many steps, a slider is held in the state in which the first surface of the slider faces upward. Conventionally, methods in which the top surface of the layers faces upward have often been used giving priority to convenience in checking the slider numbers, because the slider number needs to be frequently checked. However, in the present embodiment, the slider numbers, which are written on the top surface of the layer, can be easily identified. Therefore, the need for storing the bars in the state in which the top surface of the layers faces upward is reduced, and accordingly, the bar can be stored in the state in which the first surface faces upward, which creates an advantage in the process.

Figure 6:
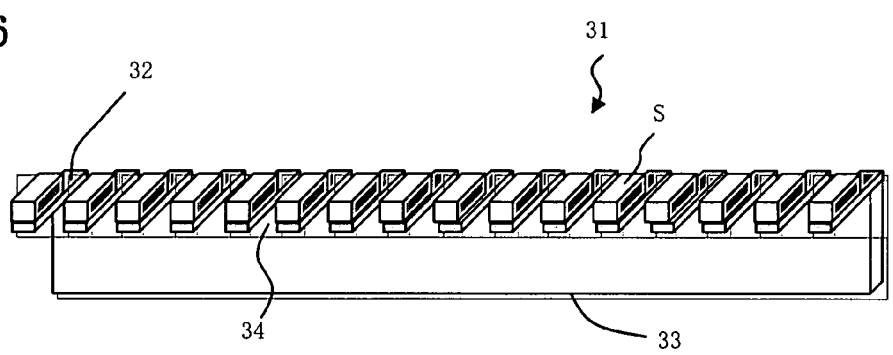
FIG. 6 is a view of a dicing jig that is used when a bar is diced into sliders.

In the above description, sliders are inspected in the state in which the sliders are included in a bar. However, sliders also can be inspected in accordance with the present invention even after the sliders are separated from a bar by means of dicing. FIG. 6 is a view of a dicing jig that is used when a bar is diced into sliders. Dicing jig 31 has support plate 33 and slider support portions 32 that are mounted perpendicularly to support plate 33. Gaps 34 are provided between slider support portions 32. The bar is fixed to dicing jig 31 with an adhesive, and is diced with a predetermined dicing tool. The space above gap 34 is used for dicing zones. The dicing tool passes through gap 34 in order to dice the bar. Each portion of the bar that has been separated, i.e., slider S, is held by slider support portion 32. Therefore, sliders S are integrated with each other via dicing jig 31 even after the bar is diced. Thus, by mounting sliders S, which are fixed to dicing jig 31, to tray 21 in the same manner as the bar described above, the same inspection method can be applied.

Figure 7:
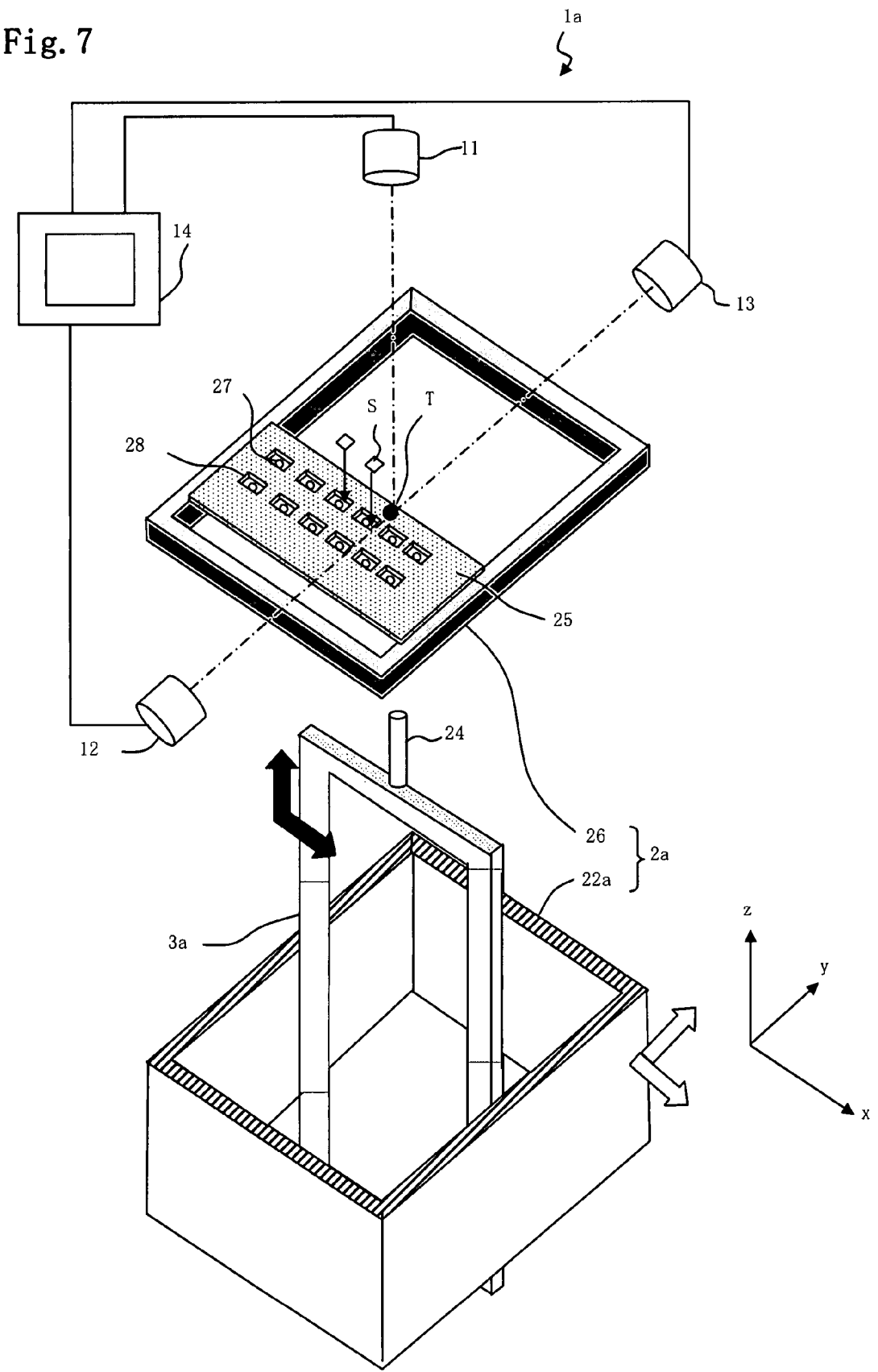
FIG. 7 is a diagram generally showing the configuration of an apparatus for inspecting a slider according to another embodiment of the present invention.

Even after the sliders are removed from the dicing jig, and are put in a completely independent state, a similar method can be applied. FIG. 7 is a diagram generally showing the configuration of an apparatus for inspecting a slider according to another embodiment of the present invention. First stage 2a includes tray support 26 for supporting slider tray 25. Slider tray 25 is provided with pockets 28 that house individual sliders. Each pocket 28 has through-hole 27 on the bottom surface thereof. Through-hole 27 is also used for drainage of cleaning water when the sliders are cleaned together with slider tray 25. Second stage 3a, which has pin 24 at the upper end, is configured to move vertically such that pin 24 abuts on the undersurface of the slider through thorough-hole 27 and such that pin 24 disengages the slider from slider tray 25 in order to move the slider upward to inspecting position T.

First camera 11 for obtaining the image of first surface M1 of the slider is provided. First camera 11 is arranged in advance such that the optical axis thereof passes through inspecting position T. Similarly, second camera 12 for obtaining the image of second surface M2 of the slider is provided. Second camera 12 is arranged in advance such that the optical axis thereof passes through inspecting position T. Further, third camera 13 for obtaining the image of third surface M3 of the slider is provided. Third camera 13 is arranged in advance such that the optical axis thereof passes through inspecting position T. Each of cameras 11-13 is connected to image display device 14. Cameras 11-13 and image display device 14 have the same configurations as those in the embodiment described above.

In order to inspect the slider, the slider is disengaged from slider tray 25 and is moved upward by causing pin 24 of second stage 3a to abut on the undersurface of the slider, which is stored in slider tray 25, through through-hole 27 formed on the bottom surface, and by moving second stage 3a upward. Operations of obtaining the images by means of cameras 11-13 and of displaying the images on image display device 14 are performed in the same manner as in the above described embodiment.

Although certain preferred embodiments of the present invention have been shown and described in detail, it should be understood that various changes and modifications may be made without departing from the spirit or scope of the appended claims.

What is claimed is:

1. A method for inspecting a slider having a substantially rectangular parallelepiped shape, comprising:
a lifting step of lifting said slider upward and stopping said slider at an inspecting position while supporting said slider at an undersurface of said slider, wherein said undersurface is a surface that is other than a first surface, said first surface being an air bearing surface or a surface that is to be formed in said air bearing surface; and
an inspection step of simultaneously inspecting said first surface and a second surface of said slider, said second surface being a surface that is other than said first surface and said undersurface, wherein said first surface is inspected by a first camera, said first camera being arranged in advance such that an optical axis of said first camera passes through said inspecting position, and wherein said second surface is inspected by a second camera, said second camera being arranged in advance such that an optical axis of said second camera passes through said inspecting position.

2. The method according to claim 1, wherein said inspection step comprises simultaneously inspecting said first surface and a third surface of said slider, said third surface being a surface that is other than said first surface, said undersurface, and said second surface,
wherein said first surface is inspected by said first camera, and
wherein said third surface is inspected by a third camera, said third camera being arranged in advance such that an optical axis of said third camera passes through said inspecting position.

3. The method according to claim 1,
wherein said lifting step comprises moving an assembly of said sliders upward and stopping said assembly at said inspecting position, wherein said sliders are aligned in a longitudinal direction of said assembly,
said method further comprising, after said inspection step;
a step of moving said assembly in the longitudinal direction of said assembly so that a slider that has not yet been inspected moves to said inspecting position, and
repeating said inspection step for said slider which moves to said inspecting position.

4. The method according to claim 3, wherein said assembly is a bar in which a plurality of sliders are formed.

5. The method according to claim 4,
wherein said lifting step comprises; disengaging said bar from a support element and lifting said bar upward by causing a moving stage to abut on an undersurface of said bar and by moving said moving stage upward, wherein said bar is only supported on said support element at both end portions of said bar by self weight thereof, and wherein said method further comprises; a step of lowering said moving stage and causing said bar to be supported on said support element after said inspection step.

6. The method according to claim 3, wherein said assembly has a plurality of sliders which are separated from a bar by means of dicing, said bar having a plurality of sliders, wherein said sliders are held together by a dicing jig after dicing.

7. The method according to claim 1, wherein said lifting step comprises disengaging said slider from a tray in which said slider is stored and lifting said slider upward by causing a moving stage to abut on said undersurface of said slider and further by moving said moving stage upward, wherein said tray has a through-hole on a bottom surface thereof, and wherein said moving stage abuts on said undersurface of said slider through said through-hole, and wherein said method further comprises a step of lowering said moving stage and storing said slider in said tray after said inspection step.

8. The method according to claim 1, wherein said inspection step comprises simultaneously displaying said surfaces of said slider on a single image display device, said surfaces being simultaneously inspected.

9. The method according to claim 1, wherein said slider is supported so that said first surface faces upward.

10. The method according to claim 1, wherein said slider is supported such that said second surface corresponds to a surface on which a slider number is written.

11. An apparatus for inspecting a slider, comprising:

a first stage which includes a support element, wherein a bar can only be supported on said support element at both end portions thereof by self weight of said bar, wherein said bar includes a plurality of sliders which are aligned in a longitudinal direction of said bar;

a second stage which is vertically movable such that said second stage abuts on an undersurface of said bar from below in order to disengage said bar from said support element to lift said bar upward to an inspecting position;

a first camera for obtaining an image of a first surface of said slider, said first surface being an air bearing surface or a surface that is to be formed in said air bearing surface, wherein said first camera is arranged in advance such that an optical axis thereof passes through said inspecting position; and a second camera for obtaining an image of a second surface of said slider, said second surface being a surface that is other than said first surface and said undersurface, wherein said second camera is arranged in advance such that an optical axis thereof passes through said inspecting position.

12. The apparatus according to claim 11, further comprising:

a third camera for obtaining an image of a third surface of said slider, said third surface being a surface that is other than said first surface, said undersurface, and said second surface, wherein said third camera is arranged in advance such that an optical axis of said third camera passes through said inspecting position.

13. The apparatus according to claim 11, further comprising:

an image display device which is configured to simultaneously display said images which are obtained by said cameras.

14. The apparatus according to claim 11, wherein said first camera has more than one magnification.

15. The apparatus according to claim 11, wherein said support element has step portions which allows said bar to rest.

16. The apparatus according to claim 11, wherein said support element is configured to support said bar such that said first surface faces upward.

17. The apparatus according to claim 11, wherein said first and second stages are configured to travel a same distance in the longitudinal direction of said bar.

18. The apparatus according to claim 17, wherein said support element is configured to hold a plurality of bars such that said bars are held in parallel with each other, and said first stage is configured to move in a direction that is perpendicular to said longitudinal direction in a horizontal plane.

19. An apparatus for inspecting a slider, comprising:

a tray for storing a slider, said tray including a through-hole on a bottom surface thereof;

a moving stage which is vertically movable such that said moving stage abuts on an undersurface of said slider through said through-hole in order to disengage said slider from said tray to lift said slider upward to an inspecting position;

a first camera for obtaining an image of a first surface of said slider, said first surface being an air bearing surface or a surface that is to be formed in said air bearing surface, wherein said first camera is arranged in advance such that an optical axis of said first camera passes through said inspecting position; and a second camera for obtaining an image of a second surface of said slider, said second surface being a surface that is other than said first surface and said undersurface, wherein said second camera is arranged in advance such that an optical axis of said second camera passes through said inspecting position.

* * * * *